(12) United States Patent
Zhang

(10) Patent No.: US 9,032,961 B2
(45) Date of Patent: May 19, 2015

(54) UNIVERSALLY ADJUSTABLE PILLOW FOR USE IN HEALTHCARE AND THERAPY

(76) Inventor: Wenbing Zhang, Nanping (CN)

( * ) Notice: Subject to any disclaimer, the term of this patent is extended or adjusted under 35 U.S.C. 154(b) by 781 days.

(21) Appl. No.: 13/142,855

(22) PCT Filed: Dec. 30, 2009

(86) PCT No.: PCT/CN2009/076227
§ 371 (c)(1),
(2), (4) Date: Jun. 30, 2011

(87) PCT Pub. No.: WO2010/075782
PCT Pub. Date: Jul. 8, 2010

(65) Prior Publication Data
US 2011/0271964 A1    Nov. 10, 2011

(30) Foreign Application Priority Data
Dec. 31, 2008  (CN) .......................... 2008 1 0072535

(51) Int. Cl.
| | |
|---|---|
| *A61G 7/07* | (2006.01) |
| *A47G 9/10* | (2006.01) |
| *A61G 13/12* | (2006.01) |
| *A47G 9/00* | (2006.01) |
| *A61F 5/56* | (2006.01) |

(52) U.S. Cl.
CPC ............ *A47G 9/10* (2013.01); *A47G 2009/005* (2013.01); *A47G 2009/006* (2013.01); *A61F 5/56* (2013.01); *A61G 7/072* (2013.01); *A61G 13/121* (2013.01); *A61G 13/1285* (2013.01); *A61G 2200/322* (2013.01)

(58) Field of Classification Search
CPC . A61G 7/072; A61G 13/121; A61G 13/1285; A61G 13/1215; A47G 9/10–9/1027; A47G 9/1081; A61F 5/56

USPC .............. 128/845, 846, 882; 5/636, 637, 639, 5/640, 643, 644, 645, 657, 723
See application file for complete search history.

(56) References Cited

U.S. PATENT DOCUMENTS

| | | | | |
|---|---|---|---|---|
| 5,360,017 A | * | 11/1994 | Austin ............................. | 5/640 |
| 5,579,551 A | * | 12/1996 | Tommaney ...................... | 5/636 |
| 5,848,448 A | * | 12/1998 | Boyd ................................ | 5/636 |
| 6,159,169 A | * | 12/2000 | Lambden ........................ | 601/15 |
| 6,671,906 B1 | * | 1/2004 | Milligan .......................... | 5/636 |
| 7,546,651 B2 | * | 6/2009 | Groteke et al. .................. | 5/636 |
| 7,874,032 B2 | * | 1/2011 | North et al. ...................... | 5/632 |
| 8,341,784 B2 | * | 1/2013 | Scott et al. ..................... | 5/655.3 |
| 2010/0325803 A1 | * | 12/2010 | Requena .......................... | 5/640 |

FOREIGN PATENT DOCUMENTS

| | | |
|---|---|---|
| CN | 1188627 | 7/1998 |
| CN | 2930492 | 8/2007 |

* cited by examiner

*Primary Examiner* — Victoria J Hicks
*Assistant Examiner* — Kari Petrik

(57) ABSTRACT

A universally adjustable pillow for use in healthcare and/or therapy includes a base board (1), and pillows for, respectively, right lateral recumbency (4), supine recumbency (2), left lateral recumbency (5) and for the neck (3) that are arranged on said base board (1). The pillows for left and right lateral recumbency (5,4) each include an external cushion, a mechanism enabling adjustment to fit vertebral curvature (52, 42), a mechanism enabling adjustment to inhibit too great an angle of lateral tilt (53, 43) and height adjustment members (51, 41). The longitudinal axes of the pillows for left and right lateral recumbency (5, 4) are set an angles α and β to the longitudinal axis of the pillow for supine recumbency (2).

20 Claims, 4 Drawing Sheets

UNIVERSALLY ADJUSTABLE PILLOW FOR USE IN HEALTHCARE AND THERAPY

TECHNICAL FIELD

The present invention relates to a healthcare and therapeutic pillow, and more particular to a healthcare and therapeutic pillow that can be continuously adjusted in multi-direction.

BACKGROUND

Maintaining a normal biological makeup and functional status during sleep is believed very important in medical community. For example, when sleeping on one's back, if the pillow is too high, the normal bending of cervical vertebra will disappear, and the cervical vertebra will distort to an opposite direction. Accompanying the distort of cervical vertebra, the windpipe, blood vessel, muscle and ligament in the neck will all distort; the root of tongue will drop back to block air duct, so as to cause snoring and even SAS (sleep apnea syndromes). Sleeping on one's back for eight hours a day will cause many kinds of disease.

Except sleeping on one's back, one may sleep on one's left side or right side. The pillow is too high or too low is most common problem, when one sleeps on one's side, which will cause severe distortion of cervical vertebra and upper thoracic vertebra, and will cause the distortion of windpipe, blood vessel, muscle and ligament in the neck. And in this circumstance, the weight of the head and neck is mostly on the shoulder, which will cause the overstress of the shoulder and obvious displacement of the shoulder blade. Sleeping in this manner for too long will cause all kinds of disease on the neck, shoulder and back.

Besides the "decubitus" problem the medics is familiar with, maintaining one sleeping posture for a long time, especially on one's side, even if this posture is biological and functional, will cause damage to the health. The above-mentioned opinions are widely acknowledged and paid attention around the globe. Mr. Xigu from Japan described this theory in detail in his book *Xigu therapy* (Xigu Gongliang, The People's Medical Publishing House, 1986). He believes in this book that sleeping on the left side may cause heart disease, diarrhea, and so on; sleeping on the right side may cause respiratory disease, obstipation, and so on, and may have uneven leg length, uneven shoulder height, lateral curvature, inclination of pelvis, and so on at same time. Chiropractors of European and American schools also identify and take this problem seriously.

In order to maintain a normal biological makeup and functional status of human body, especially of neck, shoulder and back, during sleep, the sleeper should use low pillow or no pillow when sleeping on the back, and use high pillow when sleeping on the side; the sleeper should also ensure the time of sleeping on the left side approximately equal to the time of sleeping on the right side, and avoid sleeping in only one posture for a long time. As the requirement for the height of the pillow when people sleeping on the back and side is quite opposite, the pillow that conforms the biological structure should distinguish the supine recumbency pillow and lateral recumbency pillow.

Further, the skull of human is in ellipse shape, so when sleeping on the back, it is very hard to keep skull upright, and the skull will incline to one side and always to only one side. This will cause the twist of the cervical vertebra and imbalance growth of the skull due to asymmetry effect, which will lead to oblique of the skull (including the five organs in the face). In order to solve this problem, the skull should be fixed when lying on the back to avoid inclination.

When people sleeping on the back, the weight of the neck will make the cervical vertebra dropping down to bed so as to decrease the curvature thereof, so that people should use a column pillow to support the middle part of the cervical vertebra (It is meaningless to support the whole cervical vertebra) to cancel the weight of the neck and maintain the curvature of the cervical vertebra.

It is also not right to use pure high pillow when people sleeps on the side. Because the shoulder is wider than the wrist, when people sleeps on the side, the spine is not parallel with the bed, an angle is formed therebetween, and the spine near neck is higher than the spine near wrist. When people sleeps on the side, the slant angle of the spine is the angle between the spine and the projection line thereof to the bed, which is somewhere between 5 and 25. In order to comply with the slant angle of the spine, the surface of the side sleep pillow should incline forwardly to make a "spine complying angle", which is equal to the slant angle of the spine (about 5 to 25), so as to avoid the spine, especially cervical vertebra to distort.

When people sleep on the side, people intend to sleep on the side excessively. The reason is that when people sleeps on the side, people are used to put the arm and leg on one side in front of the body, which will drag the body to twist forward, so as lead to excessive side sleep. In this posture, the harm is obvious. Not only the heart and lung are stressed, but also the shoulder contacting to the bed is excessively stressed and the shoulder joint is excessively folded inwardly, which will cause a chronic damage of the joints around the shoulder and soft tissue, block of blood circulation in upper limb, and damage to nerves in upper limb. In order to correct excessive side sleep, the side sleep pillow should have a "mechanism inhibit too great an angle of lateral tilt", which made an angle ranging from 0 to 15, to adjust the side sleep amplitude of the head, so that the face of sleeper slightly bends backwardly to effectively restrain the excessive side sleep of the whole body and to avoid the head of sleeper falling backwardly and downwardly along the surface of the side sleep pillow.

When people rolls over from the back sleep to side sleep, one must bend one's pelvispelviccoxa and knees, so the knees are lifted in front of the body. According to the "reaction principle", people will move the hip backward unconsciously to keep balance so as to avoid falling down from bed, so that an angle is formed in a horizontal plane between the upper body (spine) and longitudinal axis of the bed, which is about 0 to 20 degree, and can be called as rolling angle. Therefore, the rolling angle is an angle between the projection line of spine to the bed when sleeper sleeping on the side and the projection line of spine to the bed when sleeper sleeping on the back, presented as a sharp angle. In order to comply with this angle, there should be a "rolling complying angle" between the back sleep pillow and side sleep pillow, which is an angle between the projection of longitudinal axis of side sleep pillow and back sleep pillow to a horizontal plane, and also can be described as an angle between the projection of inner edge of side sleep pillow and outer edge back sleep pillow to the horizontal plane. The rolling complying angle is equal to the rolling angle, which is about 0 to 20. The rolling complying angle enables the upper body (spine) vertical to the pillow (in a horizontal plane) during side sleep and the shoulder near the bed closely to the pillow, so as to avoid the head away from the pillow and hanging in the air.

When people sleeps on the side, some people with shorter neck, or with shrugged shoulder, can only lay the upper part of head on the pillow and will uncomfortable hang lower part of his head in the air, due to the slant angle of the spine, because his shoulder near bed is against the pillow. In order to solve this problem, it is necessary to enlarge the space between the shoulder near bed and the side sleep pillow so as to receive the over high shoulder and increase the contact area of the surface of side sleep pillow and the head so as to fully support the head.

Therefore, in order to conform to the biological structure no matter during side sleep and back sleep, it is necessary to distinguish the back sleep pillow and side sleep pillow, so as to avoid inclination of the head, comply with the slant angle of the spine during side sleep, and correct excessive side sleep. Further, a rolling complying angle should be provided to avoid head being away from pillow when turning over the body, the space between the shoulder and side sleep pillow should be enlarged, and the contact area of the surface of side sleep pillow and the head.

For the sake of illustration, "front", "back", "left", "right", "up", and "down" refer to the direction of the standing object.

A Chinese patent entitled Adjustable combined cervical vertebra pillow (Publication number CN1188627A) comprises a unit freely combined by a neck pillow, back sleep pillow, right lateral recumbency pillow and left lateral recumbency pillow, and an outside pillowslip. The back head pillow and the neck pillow in front thereof constitute a middle part of adjustable combined cervical vertebra pillow, for back sleep. The right lateral recumbency pillow is on the right of the middle part, for right side sleep. The left lateral recumbency pillow is on the left of the middle part, for left side sleep. The back head pillow, right lateral recumbency pillow and left lateral recumbency pillow are all composed by a stack of rectangular soft slices tied via a nylon fastener tape. Apparently, the height of the back head pillow, right lateral recumbency pillow and left lateral recumbency pillow can be adjusted by the number of the slice. The middle part is higher than the left and right side. The neck pillow is in column shape and transversely placed. It composed by curling a rectangular soft slice and fastened via a nylon fastener tape. The size can be adjusted by the number of the slices. The drawback is that it can only adjust the height of the back head pillow, left pillow and right pillow.

Further, a Chinese patent entitled Functional pillow with adjustable height (Publication number CN2930492Y) comprises an upper pillow panel, screw, inner gear sleeve, outer gear sleeve, and lower pillow panel; the lower surface of the upper pillow panel connects to the top of the inner gear sleeve, the outer gear sleeve engages with the screw, and the seat for fixing the screw is fastened with the lower surface of the lower pillow panel. The height of the Functional pillow with adjustable height can be adjusted by spinning the screw. The pillow inlet is of S-shape, and put on the entire upper pillow panel. It has the advantage of adjustable height, and adjustable slant angle of the upper pillow surface. However, the drawback is that there is no difference between the back sleep pillow and side sleep pillow when adjusting the height and slant angle, and the range of adjusting angle is only from 0 to 6, which is very small, so that the problem brought by slant angle of spine during side sleep can not be solved. Further, it is not considered that when sleeper turns back sleep to left or right side sleep, the head cannot fully contact with pillow, and it is not considered how to prevent excessive side sleep.

SUMMARY

An object is to provide a universally adjustable pillow for use in healthcare and/or therapy A universally adjustable pillow for use in healthcare and therapy includes a base board, and pillows for respectively, right lateral recumbency, supine recumbency, left lateral recumbency and for the neck that are arranged on said base board. While the right lateral recumbency pillows is on the right side of the supine recumbency pillows the left lateral recumbency pillows on the left side and the neck pillow on the front of the supine recumbency pillows. Both the left and right lateral recumbency pillows include several pieces of connected height adjustment members to adjust the height of it. A mechanism enabling adjustment to fit vertebral curvature to adjust the front slant angle of the surface of the lateral recumbency pillows and/or the front slant angle of the lateral recumbency pillows or the anteflexion angle and anteflexion position of lateral recumbency pillows, a mechanism enbling adjustment to inhibit too great an angle of lateral tilt. The longitudinal axes of the pillows for left and right lateral recumbency are set at angle to the longitudinal axis of the pillow for supine recumbency. And the angle is X20 degree.

This invention of bi-use pillow also includes right and left side slide stop to prevent the sleeper from dropping from the pillow. These two slide stops are glued on the inner side on the surface of the right and left lateral recumbency pillow respectively.

The supine pillow mentioned in this invention includes 0-3 pieces of height adjustment members each with the thickness of 1 cm-4 cm and an external cushion. And on the upper and bottom side of every said height adjustment members there is an adhesive wear for aligning and mounting them together. The external cushion has adhesive on the bottom to which glue the most upper height adjustment member. And the bottom height adjustment member is glued to the base board through the adhesive wear. The external cushion is made up of sponge thick of 2 cm with a removable and washable cloth or towel cover. And the adhesive wear is sewn on the bottom of the cloth or towel cover. On the surface of the supine pillow there are two fixation cushions to avoid the head turning aside which was set in trapezoidal form. The two fixation cushions are 10 cm long and the cross-section of which is a right triangle with a 6 cm bevel edge. The two fixation cushions are glued on the surface of the supine pillow through adhesive wear.

The neck pillow mentioned in this invention includes 0-3 pieces of height adjustment members each with the thickness of 1-4 cm and a neck pillow column. The upper part of the neck pillow column is a half cylinder and the bottom part is a pillar. The height adjustment members are glued to each other through the adhesive wear at the upper and bottom side of each member. The upmost height adjustment member is adhering to the bottom of the neck pillow column and the undermost height adjustment member is adhering to the base board through adhesive wear. The neck pillow also includes neck pillow external cushion which is fixed on the surface, front and rear of the half cylinder of the neck pillow column. The length of the neck pillow column is 15 cm. The width*height of the bottom pillar is 4 cm*2 cm. The radius of the cross-section of the half cylinder on the neck pillow column is 2 cm. And the area of the neck pillow height adjustment member is 15 cm*6 cm.

The height adjustment members of both the right and left lateral recumbency pillow in this invention include 0-4 pieces of height adjustment members each with a height of 1 cm-5 cm respectively. The height adjustment members of the lateral recumbency pillows are glued together through the adhesive wear on the upper and bottom side of each members and the undermost height adjustment member is glued to the base board through the adhesive wear on the bottom side of it.

The mechanism enabling adjustment to fit the vertebral curvature and the mechanism enabling adjustment inhibit too great an angle of lateral tilt of the right and left lateral recumbency pillows are carried out through angle adjustment bar set and supporting bar set.

Thereof the mechanism enabling adjustment to fit the vertebral curvature includes base board, working panel, hinge, and angle bar set. Between the front edge of the base board and the front edge of the working panel there are two hinges. And an angle adjustment bar is at back between the base board and working panel. The angle adjustment bar is parallel with the back edge of the base board. The mechanism enabling adjustment inhibit too great an angle of lateral tilt on the right and left lateral recumbency pillows include base board, working panel, hinge and angle adjustment bar. Between the inner edge of the base board and working panel there are two hinges. And an angle adjustment bar is set near the outside edges of and between the base board and working panel. The angle adjustment bar is parallel with the outside edge of the base board.

The supporting bar mechanism enabling adjustment to fit the vertebra curvature on the right and left lateral recumbency pillows includes base board, working panel, hinges, supporting bar and fastening screws. Thereof two hinges are mounted at the front edge between the base board and working panel. The arch section of the supporting bar is fastened on the bottom of the working panel. A slot is cut along the centerline of the arch section for the fastening screw to screw through. The nailhead of the fastening screw can be resembled and dissembled by hand and the nailhead is fastened on the rear of the base board. The supporting bar mechanism enabling adjustment inhibit too great an angle of lateral tilt on the right and left lateral recumbency pillows include base board, working panel, hinges, supporting bar and fastening screw. Two hinges are mounted on the inner sides of and between the base board and working panel. The arch section of the supporting bar is fastened on the bottom of the outer side of the working panel. A slot is cut along the centerline of the arch section for the fastening screw to screw through. The nailhead of the fastening screw can be resembled and dissembled by hand and the nailhead is fastened on the outer side of the base board.

The mechanism enabling adjustment to fit the vertebra curvature in this invention can be glued between the lateral recumbency pillows' height adjustment members and the mechanism enabling adjustment to inhibit too great an angle of lateral tilt, or between the base board and the lateral recumbency pillows' height adjustment members, or between any of the two lateral recumbency pillows' height adjustment members. In a preferred embodiment, the angle adjustment bar of the mechanism enabling adjustment to fit the vertebra curvature is glued on the surface of base panel and the bottom side of the working panel of the mechanism. And the angle adjustment bar of the mechanism enabling adjustment to inhibit too great an angle of lateral tilt is glued on the surface of the base panel and the bottom side of the working panel of the mechanism. In an another preferred embodiment of this invention a guide is mounted vertically under the angle adjustment bar of the mechanism enabling adjustment to fit the vertebra curvature and mechanism enabling adjustment to inhibit too great an angle of lateral tilt respectively. Correspondingly a notch is cut on the surface of the base panel of the mechanism enabling adjustment to fit the vertebra curvature and the mechanism enabling adjustment to inhibit too great an angle of lateral tilt respectively. The guides are embedded in the notch and can slide freely. And the top of the angle adjustment bar is adhering to the bottom of the working panel of the two said mechanisms respectively.

The mechanism enabling adjustment to fit the vertebra curvature and the mechanism enabling adjustment to inhibit too great an angle of lateral tilt of the right and left lateral recumbency pillows in this invention of bi-use pillow are performed through angle adjustment set and supporting bar set. Thereof the angle adjustment bar set of the mechanism enabling adjustment to fit the vertebra curvature of the right and left lateral recumbency pillows includes base board, working panel, hinge and angle adjustment bar. Thereof the base board is adhering to the height adjustment members through adhesive wear. Two hinges are mounted between the front edges of the base board and said working panel. And at the back between the base board and the working panel lay the angle adjustment bar which is parallel with back edge of the base board.

The angle adjustment bar set of the mechanism enabling adjustment to inhibit too great an angle of lateral tilt includes working panel, hinge and angle adjustment bar. The inner edge of the working panel and the inner edge of said working panel of the mechanism enabling adjustment to fit the vertebra curvature are connected by hinge. And between the outer sides of the working panel of the mechanism enabling adjustment to fit the vertebra curvature and the working panel of the mechanism enabling adjustment to inhibit too great an angle of lateral tilt set an angle bar which is parallel with the outer edge of the working panel of the mechanism enabling adjustment to fit the vertebra curvature.

The supporting bar set of the mechanism enabling adjustment to fit the vertebra curvature of the right and left lateral recumbency pillows include base board, working panel, hinge, supporting bar and fastening screw. Thereof the base board and the height adjustment members are fixed together through adhesive wear. Two hinges was mounted on the front edges of the base board and the working panel. The arch section of the supporting bar was fixed on the bottom panel at the back of the working panel. A slot is cut along the centerline of the vertical arch section of the supporting bar for the fastening screw to screw through. The fastening screw has a nailhead which can be removed and mounted by hand and the nailhead is fastened at the rear of the base board.

The supporting bar set of the mechanism enabling adjustment to inhibit too great an angle of lateral tilt of the right and left lateral recumbency pillows include working panel, hinge, supporting bar and fastening screw. The inner edge of the working panel of the mechanism enabling adjustment to inhibit too great an angle of lateral tilt and the inner edge of working panel of the mechanism enabling adjustment to fit the vertebra curvature are connected by hinge. The arch section of the supporting bar is fixed on the bottom of the outer side of the working panel. A slot is cut along the centerline of the vertical arch section of the supporting bar for the fastening screw to screw through. The fastening screw has a nailhead which can be removed and mounted by hand and the nailhead is fastened on the outer side of the working panel of the mechanism enabling adjustment to fit vertebra curve.

In a preferred embodiment of this invention, the angle adjustment bar of the mechanism enabling adjustment to fit the vertebra curvature is glued through adhesive wear between the surface of the base board and the bottom of the working panel of the mechanism enabling adjustment to fit the vertebra curvature. And the angle adjustment bar of the mechanism enabling adjustment to inhibit too great an angle of lateral tilt is glued through adhesive wear between the surface of the working panel of the mechanism enabling adjustment to fit the vertebra curvature and the bottom of the working panel of the mechanism enabling adjustment to inhibit too great an angle of lateral tilt.

In another preferred embodiment, a guide is set vertically under the angle adjustment bar of the mechanism enabling adjustment to fit vertebra curvature and the mechanism enabling adjustment to inhibit too great an angle of lateral tilt respectively. Correspondingly a notch is cut on the base board and the surface of working panel of the mechanism enabling adjustment to fit the vertebra curvature. And the guide is embedded in the notch in which it can slide freely. The top of the angle adjustment bars of the mechanism enabling adjustment to fit the vertebra curvature and the mechanism enabling adjustment to inhibit too great an angle of lateral tilt are glued through adhesive wear to the corresponding bottom of the working panels of the two said mechanisms.

In this invention of bi-use pillow, the adjustable range of the mechanism enabling adjustment to fit the vertebra curvature is 5-25 degree, and the adjustable range of the mechanism enabling adjustment to inhibit too great an angle of lateral tilt is 0-15 degree.

In this invention, the external cushion of the right and left lateral recumbency pillows is comprised of upper and lower layer each with thickness of 2.5 cm. A velvet or towel cover is set outside the overlapped upper and lower layer of the cushion. The adhesive wear is sewing on the bottom of the cover. The external cushion is adhering to the mechanism enabling adjustment to inhibit too great an angle of lateral tilt through its adhesive wear at the bottom. The adhesive wear in this invention of bi-use pillow is a hook and loop fastener.

In this invention of bi-use pillow, there is a rounded rectangle of 8 cm*6 cm on the external cushion of the right and left lateral recumbency pillows respectively for ears to put in.

In this invention of bi-use pillow, the size of the height adjustment members of the right and left lateral recumbency pillows is 20*20 cm$^2$. The size of the base board and the working panel of the mechanism enabling adjustment to fit the vertebra curvature is 20*20 cm$^2$ with a thickness of 2 cm. The size of the base board and working panel of the mechanism enabling adjustment to inhibit too great an angle of lateral tilt is 20*20 cm$^2$ with a thickness of 2 cm. The size of the external cushion is 20*20 cm2. In this invention of bi-use pillow, a pressure sensor can be attached to the right and left lateral recumbency pillows to sense the lateral condition of the sleeper. And also a timer is attached to the bi-use pillow to accumulate the time the sleeper rest on right lateral recumbency pillows and the left lateral recumbency pillows respectively. And according to the difference in time a sound LCD instructor can provide guidance for the sleeper. The pressure sensor, electronic timer and sound and light electronic instructor can be control by a microcomputer. The sound LCD instructor includes speaker and LCD. The speaker is mounted in the rounded rectangle on the external cushion for putting ears.

This invention has the following advantages.

1) The right lateral recumbency pillows, supine recumbency pillows, neck pillow and left lateral recumbency pillows are all fixed on the base board through the hook and loop fastener. The position of and the spacing between the pillows and the right and left lateral rolling angle of the left and right lateral recumbency pillows can be easily adjusted by staggering the relative position of the hook and loop fastener. This invention can be used by different sleepers of maximum body types. When the sleeper rolling laterally to the side to change sleeping position the lateral recumbency pillows can still fit the head to maximum degree. The neck pillow can be freely adjusted back and forth to point to the cervical joints need adjust precisely. Each pillow can be used alone and can be combined together to achieve maximum benefits.

2) The height of all the right lateral recumbency pillows, supine recumbency pillows, neck pillow and left lateral recumbecy pillows can be adjusted by adhesive wear. The proper height can be achieved through removing or assembling the corresponding height adjustment members in order to fit the different requirement of different body part of different sleepers in different sleeping position. So as to make the neck and head comfortable in lateral and supine position, release the pressure on the shoulder and make sure of without distorting the spine and shifting the shoulder blade and to guarantee the obstructed blood circulate well in every organ. This invention can improve the sleeping quality of the sleeper and make the sleeper sleep in a good biological functional condition.

3) There are two fixation cushions on the surface of the supine pillow to maintain the head straight and not dropping to the left and right side. The position, space and the angle between the two fixation cushion can be adjusted to fit the head types of different sleepers 4) There are mechanisms enabling adjustment to fit the vertebra curvature in the right and left lateral recumbency pillows to fit the vertebra curvature when the sleeper sleeps on the side. Furthermore, there are two ways to change the position of the lateral recumbency pillows and make it totally incline forward or partly incline forward and/or partly move forward to enlarge the space between the shoulder on the bed and the lateral recumbency pillows and increase the contact area between the head and the surface of the lateral recumbency pillows in order to bear the weight of the head more completely. One way is to change the position of the mechanism enabling adjustment to fit the vertebra curvature in the lateral recumbency pillows. The other way is to stagger one or more members of the lateral recumbency pillows with the reference to the other members under it.

5) A mechanism enabling adjustment to inhibit too great an angle of lateral tilt is mounted in the right and left lateral recumbency pillows respectively in order to make the lateral recumbency pillows to incline inwardly. And the slant angle can be adjusted from 0-15 degree.

6) There is a rounded rectangle on the external cushion of the right and left lateral recumbency pillows respectively to release the pressure of the ear and make the tissue around ear bear the weight of the head evenly.

7) A pressure sensor is mounted in lateral recumbency pillows to sense and accumulate the time sleeper rest on the left and right recumbency pillows. And according the result of the timer guidance can be provided to different sleeper on how to use the lateral recumbency pillows to avoid sleeping on one side for too long and can be used to cure the diseases caused by sleep on one side for long period.

8) The material of this bi-use pillow is cheap and easy to find include plank stuff, cloth, sponges, a bit of common metal components which are harmless to the body. With these simple materials a universally adjustable pillow for use in healthcare and therapy can be made to guarantee the sleeper's sleep quality comprehensively and achieve the efficient use of natural material which is environment friendly.

DETAILED DESCRIPTION OF EMBODIMENTS

Embodiment 1

Universally Adjustable Pillow for Use in Healthcare and Therapy

Figure 1:
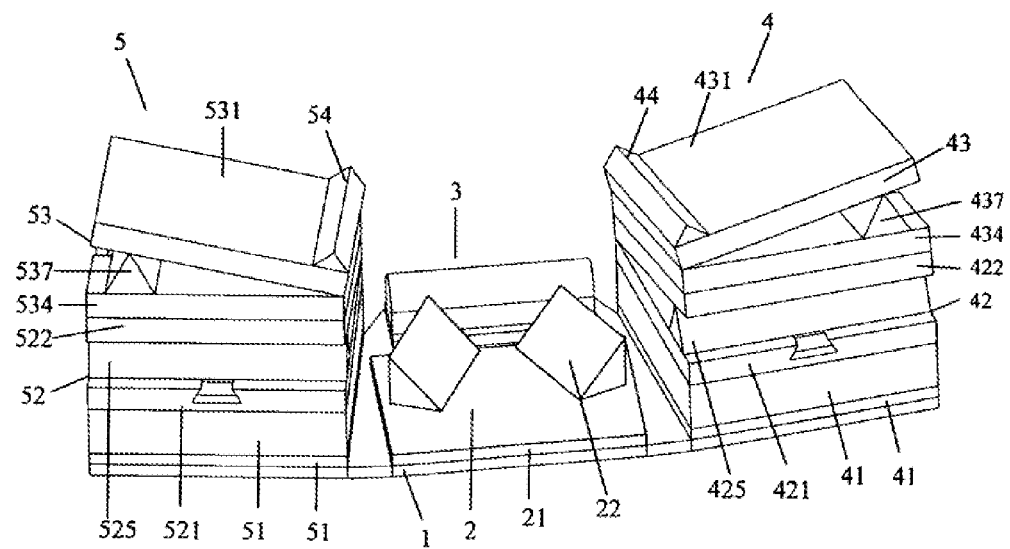
FIG. 1 is the schematic of the angle adjustment bar set in this invention viewed from the back.

As shown in FIG. 1, this invention of universally adjustable pillow for the use in healthcare and therapy include base board (1), right lateral recumbency pillows (4), left lateral recumbency pillows (5), supine recumbency pillows (2) and neck pillow (3).

1.1 Base board

Figure 2:
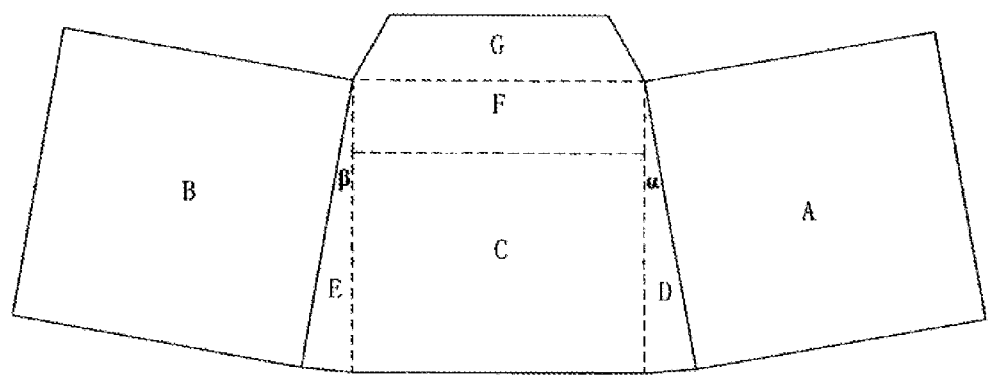
FIG. 2 shows the distribution of the adhesive wear on the base boards of the right lateral recumbency pillows, supine recumbency pillows, left lateral recumbency pillows and neck pillow in the preferred embodiment of this invention.

As shown in FIG. 2, base board (1) is 1 cm thick and include area A, B, C, D, E, F, G. Thereof area A, B and area C+F are squares. Area C is a rectangle of size 20*15 and area F is a rectangle of size 20*5. Area G is a isosceles trapezoid whose dimensions are top=15 cm, bottom=20 cm, height=4.5 cm. The angle $\alpha=\beta=10$. Area A is the adhesion area of right lateral recumbency pillow (4); Area B is the adhesion area of the left lateral recumbency pillow (5); Area C+F is the adhesion area of the supine recumbency pillow (2); Area F+G is the adhesion area of the neck pillow (3); Area F is the overlap of adhesion area of neck pillow (3) and supine pillow (2) on the base board (1). Area D and E is the gap region. Between the inner edge of area A and the right edge of area C+F there is a rolling angle $\alpha$ and between the inner edge of area B and the left edge of the area C+F there is a rolling angle $\beta$.

The above mentioned adhesion areas and the angles are pre-set which can be adjusted through stagger the pillows back and forth or rotate the pillows before re-adhere according to practical requirements. So the adhesion position and the angle may not be necessarily adopted in practical use.

Adhesive wear such as hook and loop fasteners of different colors can be nailed on the four corners, middle or edges of base board with tacks etc. in order to glue the right lateral recumbency (4) supine pillow (2), neck pillow (3), left lateral recumbency (5) and make the pillow easy to use. Same purpose can be achieved by choosing adhesive hook and loop fasteners to glue directly on the just mentioned areas on the base board.

1.2 Supine Recumbency Pillow

Shown as in FIG. 1, the supine recumbency pillow (2) in this invention of bi-use pillow includes height adjustment members (21) and one external cushion (figure not shown). The height adjustment members and the external cushion of the supine recumbency pillow both are rectangle size of 20 cm*15 cm. Thereof the height adjustment members (21) include plank stuff thick of 1-4 cm with the hook and loop fastener on both the top and bottom. 0 to 3 pieces of height adjustment members (21) can be stacked together and glue on area C+F on the base board (1) to adjust the height of the supine recumbency pillow (2) and the adjustable height range is 0-7 cm. The external cushion is a 2 cm thick sponge with a removable and washable cloth or towel cover at the bottom of which sewing the hook and loop fastener. When the height adjustment member (21) is not needed the external cushion can be glue directly on area C+F of the base board. The supine recumbency pillow (2) adjoins the back of neck pillow (3) and glue on the area C+F of the base board (1) in practical use. When the neck pillow (3) is moved back and forth, the supine pillow (2) is moved correspondingly of the same distance to the same direction.

On the surface of the supine recumbency pillow (2) two extra fixation cushions (22) can be added to fix the sleeper's head. The fixation cushion (22) is 10 cm long with a cross-section of isosceles right triangle or right triangle with an acute angle of 60 degree. The hypotenuse of the right angle is 6 cm long and can be made in a concave arch shape to fit the head of the sleeper. The fixation cushion (22) is made of a piece of sponge with a cloth or towel cover and is glued on the surface of the supine recumbency pillow (2) with the hook and loop fastener on the bottom of the cover. The two hypotenuse of the right angle is pointing to each other in a shape of trapezoidal viewed form behind and above or viewed along the axis of the base board. The two fixation cushions (22) in trapezoidal shape are located in the center of the supine recumbency pillow (2) and can be moved along the vertical axis of the supine pillow. The distance and angle between the two fixation cushions (22) can be adjusted according to the requirement. The sleeper can lean his head on the two hypotenuses of the cushions in order to maintain the head in a straight position and to prevent the head tilt aside. The sense of stability can be improved in this way.

1.3 Neck Pillow

Figure 3:
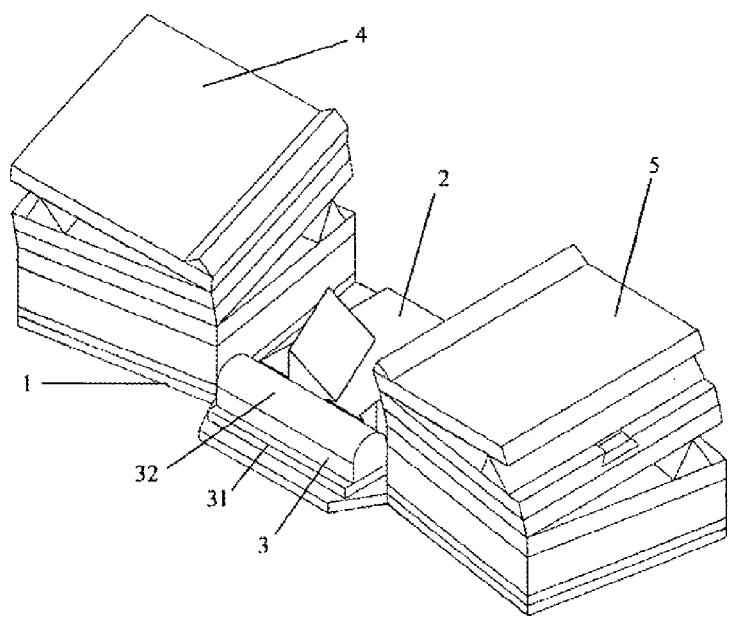
FIG. 3 is the schematic of the angle adjustment bar set in the bi-use pillow viewed from the front left.

As showed in FIG. 3, the neck pillow mentioned in this invention includes 3 pieces of height adjustment members (31) each with the thickness of 1-4 cm, a neck pillow column and an external cushion (figure not shown). The height adjustment members (31) are rectangles of a size 6 cm*15 cm. At the top and bottom of each height adjustment members there are the hook and loop fasteners. 0-3 pieces of the height adjustment members (31) are stacked together and glued on the area F+G of the base board (1) according to the requirements to adjust the height of the neck pillow. The adjustable height range of the neck pillow is 0-7 cm. The upper part of the neck pillow column is a half cylinder and the bottom part is a pillar. The radius of the cross-section of the half cylinder is 2 cm. The cross-section of the bottom pillar is a rectangle size of 4 cm*2 cm. The neck pillow column (32) can be made of slightly harder materials such as EVA, plastic, wood etc. The neck pillow also includes a cloth or towel cover. The hook and loop fastener is sewn on the surface, front and rear of the cover. The cover is glued on the surface of the height adjustment members (31) through the hook and loop fastener on its bottom. When the height adjustment members is no longer needed the neck pillow column can be glued on the area of F+G of the base board directly. The external cushion (figure not shown) of the neck pillow is made of high-density sponge 2-4 cm thick and 15 cm wide. A cloth or towel cover is put on the sponge. The hook and loop fastener is sewn on the bottom of the external cushion through which the external cushion can cover the surface of the half cylinder of the neck pillow column perfectly. If the neck pillow column is made of sponge with high hardness the cross-section of the neck pillow column can be enlarged accordingly while the length of column remains 15 cm. In this case the external cushion can be removed.

1.4 Lateral Recumbency

As shown in FIGS. 1, 3, 6 and 7, the lateral recumbency pillow (5,4) include 4 pieces of height adjustment members (51,41), a mechanism enabling adjustment to fit the vertebra curvature (52,42), a mechanism enabling adjustment to inhibit too great an angle of lateral tilt (53,43) and a external cushion (figure not shown). All the above mentioned components are square with sides of 20 cm.

The height adjustment member (51, 41) is made of plank stuff 1 cm-5 cm thick. At the top and bottom of each height adjustment members there is the hook and loop fastener. 0-4 pieces of height adjustment members (51, 41) can be stacked together and glued on area B and A of the base board according to requirements in order to adjust the height of the lateral recumbency pillows. The adjustable height range is 0-12 cm which can be enlarged by increasing the number of the height adjustment members.

Mechanism enabling adjustment to fit vertebra curvature (52, 42) includes a base board (521,421), and working panel (522,422) and two hinges (figure not shown). The thickness of both the base board (521,421) and working panel is 2 cm. Two hinges are mounted between the front edges of the base board (521,421) and working panel (522,422). The angle between the base board (521,421) and the working panel (522,422) can be adjusted by changing the distance between the back edges of the base board (521,421) and the working panel (522,422). The adjustable angle range is 5-25 degree. The mechanism enabling adjustment to fit vertebra curvature is glued on the top of the height adjustment members (51,41) through the hook and loop fastener on the bottom of the base board (521,421) and the hook and loop fastener on the surface of the adjustment members (51,41). The surface of the working panel (522,422) of the mechanism enabling adjustment to fit vertebra curvature is glued on the bottom of the base board (534,434) of the mechanism enabling adjustment to inhibit too great an angle of lateral tilt (53,43) through the hook and loop fastener. However, the mechanism enabling adjustment to fit the vertebra curvature can be set other than the position between the base board (534,434) of the mechanism enabling adjustment to inhibit too great an angle of lateral tilt (53,43) and the top of the height adjustment members (51,41). It can also be separated out and set between area B,A of the base board (1) and the bottom of the height adjustment members (51,41) of the lateral recumbency pillows or can be set between any of the two height adjustment members if necessary. Thus can make the components above the working panel (522,422) of the mechanism enabling adjustment to fit the vertebra curvature (52, 42) incline and move forward. The inclination of the lateral recumbency pillow (5,4) and the distance and angle moved forward can be adjusted by changing the position of the mechanism enabling adjustment to fit the vertebra curvature (52,42) in the lateral recumbency pillow (5,4) and the inclination of the working panel (522,422) of the mechanism.

The mechanism enabling adjustment to inhibit too great an angle of lateral tilt (53,43) include base board (534,434), working panel (531,431) and hinges (figure not shown). The thickness of both the base board (534,434) and the working panel (531,431) is 2 cm. Two hinges are mounted on the inner edges of the base board (534,434) and the working panel (531,431). The angle between the base board (534,434) and the working panel (531,431) can be adjusted by changing the distance between the outside edges of the base board (534, 434) and the working panel (531,431). The adjustable angle range is 0-15 degree. The mechanism enabling adjustment to inhibit too great an angle of lateral tilt can work without the base board (534,434) which can be replaced by the working panel (522,422) of the mechanism enabling adjustment to fit the vertebra curvature (52,42). The two hinge (figure not shown) can be mounted on the inner edges of the working panel (522,422) of the mechanism enabling adjustment to fit vertebra curvature (52,42) and the working panel (531,431) of the mechanism enabling adjustment to inhibit too great an angle of lateral tilt (53,43). A piece of plank stuff can be saved in this way, which is the base board (534,434). However, in this way the mechanism enabling adjustment to fit vertebra curvature (52, 42) can no longer be separated out and moved up and down.

The external cushion of the lateral recumbency pillow (figure not shown) has two layers. The bottom layer adopted slight harder materials such as medium density sponge etc. The upper layer adopted soft materials such as sponge etc. There is a velvet or towel cover outside the two layers of external cushion. A hook and loop fastener is sewn at the bottom of the cover by which the external cushion is glued on the working panel (531,431) of the mechanism enabling adjustment to inhibit too great an angle of lateral tilt (53,43).

Many method can be adopted to adjust the angle between base board (521,421) and working panel (522,422) of the mechanism enabling adjustment to fit vertebra curvature (52, 42) and the angle between base board (534,434) and the working panel (531,431) of the mechanism enabling adjustment to inhibit too great an angle of lateral tilt (53,43). In the following preferred embodiment, two methods will be introduced. One is realized through the "angle adjustment bar set" and the other is through "supporting bar set".

1.4.1 Angle Adjustment Bar Set

FIG. 1 and FIG. 3 show the working mechanism of the respective angle adjustment bar set of the mechanism enabling adjustment to fit the vertebra curvature (52,42) and the mechanism enabling adjustment to inhibit too great an angle of lateral tilt (53,43) of the lateral recumbency pillows.

An angle adjustment bar is placed at the back between the base board (521,421) and the working panel (522,422) of the mechanism enabling adjustment to fit the vertebra curvature (52,42) which is parallel with the back edge of the base board (521,421); An angle adjustment bar is placed at the outer side between the base board (534,434) and the working panel (531,431) of the mechanism enabling adjustment to inhibit too great an angle of lateral tilt (53,43) which is parallel with the outer edge of the base board (534,434).

The angle adjustment bar (525,425) of the mechanism enabling adjustment to fit vertebra curvature (52, 42) is 3-20 cm long. The angle adjustment bar can be categorized into 3 groups according to its height which is 1.5 cm, 2.5 cm or 4.5 cm. The cross-section of the angle adjustment bar (525,424) can be triangle, a quarter of a circle or trapezoid. The angle between the base board (521,421) and the working panel (522,422) can be adjusted by adopting angle adjustment bar of different height or by changing the distance between the angle adjustment bar (525,424) and the hinge. The adjustable angle range is 5-25 degree.

Because the mechanism enabling adjustment to fit vertebra curvature (52,42) of the left lateral recumbency pillow (5) and the right lateral recumbency pillow (4) are similar we can take the angle adjustment bar (525) in the mechanism enabling adjustment to fit vertebra curvature of the left lateral recumbency pillow (5) for example to explain the connectivity between the angle adjustment bar (525,425) and the base board (521,421) and between the angle adjustment bar (525, 425) and the working panel (522,422)

Figure 4:
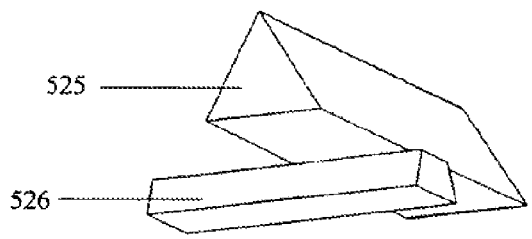
FIG. 4 is the schematic of the guide under the angle adjustment bar of the mechanism enabling adjustment to fit the vertebra curvature in the left lateral recumbency pillows.
Figure 5:
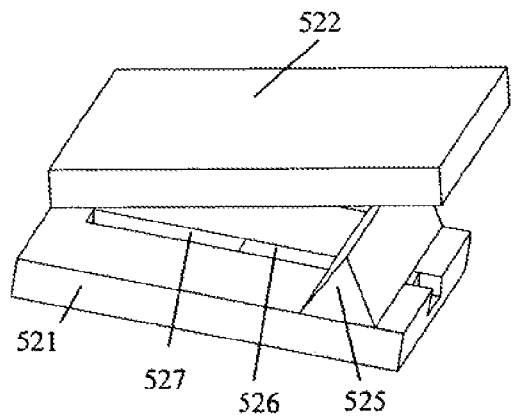
FIG. 5 is the schematic shows the match between the angle adjustment bar and the notch of the mechanism enabling adjustment to fit the vertebra curvature in the left lateral recumbency pillows.

As shown in FIG. 4, in the middle of the angle adjustment bar (525) a guide (526) is mounted under it and vertical to its axes. The cross-section of the guide (526) can be a trapezoid or in a convex shape. As shown in FIG. 5, a notch (527) is cut accordingly to the guide (526) in the middle of the base board (521) which is parallel to the outer edge of the base board (521). The guide (526) can slide in and out of the notch (527) from the back edge of the base board (521) in order to replace the angle adjustment bar (525) of different size. When the angle adjustment bar (525) slide freely along the notch (527) the distance between the bar (525) and the hinge is changing accordingly. The angle between the base board (521) and the working panel (522) can be adjusted through this guide (526) and notch (527) mechanism. The top of the angle adjustment bar (525,524) is glued to the bottom of the working panel (522,422) by the hook and loop fastener. The guide and notch mechanism between the angle adjustment bar (525,425) and the base board (521,421) can be replaced by gluing the angle adjustment bar (525,425) on the base board (521,421) by the hook and loop fastener to achieve the same purpose.

The angle adjustment bar (537,437) of the mechanism enabling adjustment to inhibit too great an angle of lateral tilt (53, 43) is 3-20 cm long. The angle adjustment bar can be categorized into 3 groups according to its height which is 0.35 cm, 1 cm or 2.5 cm. The cross-section of the angle adjustment bar (537,437) can be triangle, a quarter of a circle or trapezoid. The angle between the base board (534,434) and the working panel (531,431) can be adjusted by adopting angle adjustment bar of different height or by changing the distance between the angle adjustment bar (537,437) and the hinge. The adjustable angle range is 0-15 degree.

Similar to the setting of the angle adjustment bar (525,425) of the mechanism enabling adjustment to fit vertebra curvature (52, 42), in the middle of the angle adjustment bar (537, 437) a guide (figure not shown) is mounted under it and vertical to its axes. The cross-section of the guide can be a trapezoid or in a convex shape. A corresponding notch (527) is cut in the middle of the base board (534,434) which is parallel to the outer edge of the base board (534,434). The guide can slide in and out of the notch from the back edge of the base board (534,434) in order to replace the angle adjustment bar (537,437) of different size. When the angle adjustment bar (537,437) slide freely along the notch the distance between the bar (537,437) and the hinge is changing accordingly. The angle between the base board (534,434) and the working panel (531,431) can be adjusted through this guide and notch mechanism. The top of the angle adjustment bar (537.437) is glued to the bottom of the working panel (531, 431) by the hook and loop fastener. The guide and notch mechanism between the angle adjustment bar (537,437) and the base board (534,434) can be replaced by gluing the angle adjustment bar (537,437) on the base board (534,434) by the hook and loop fastener to achieve the same purpose.

1.4.2 Supporting Bar Set

Figure 6:
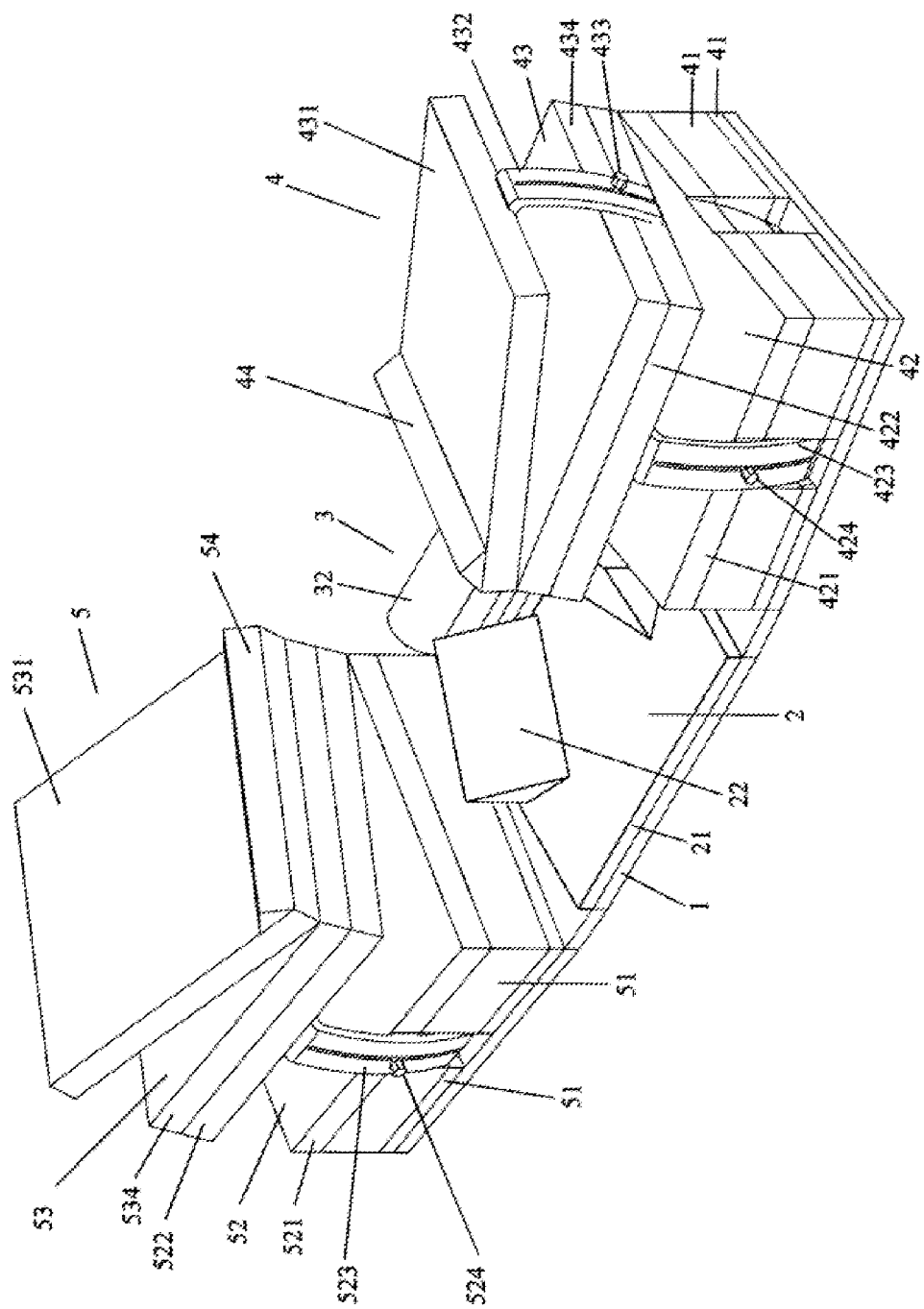
FIG. 6 is the schematic of the supporting bar set of the bi-use pillow in this invention viewed from the right back direction.
Figure 7:
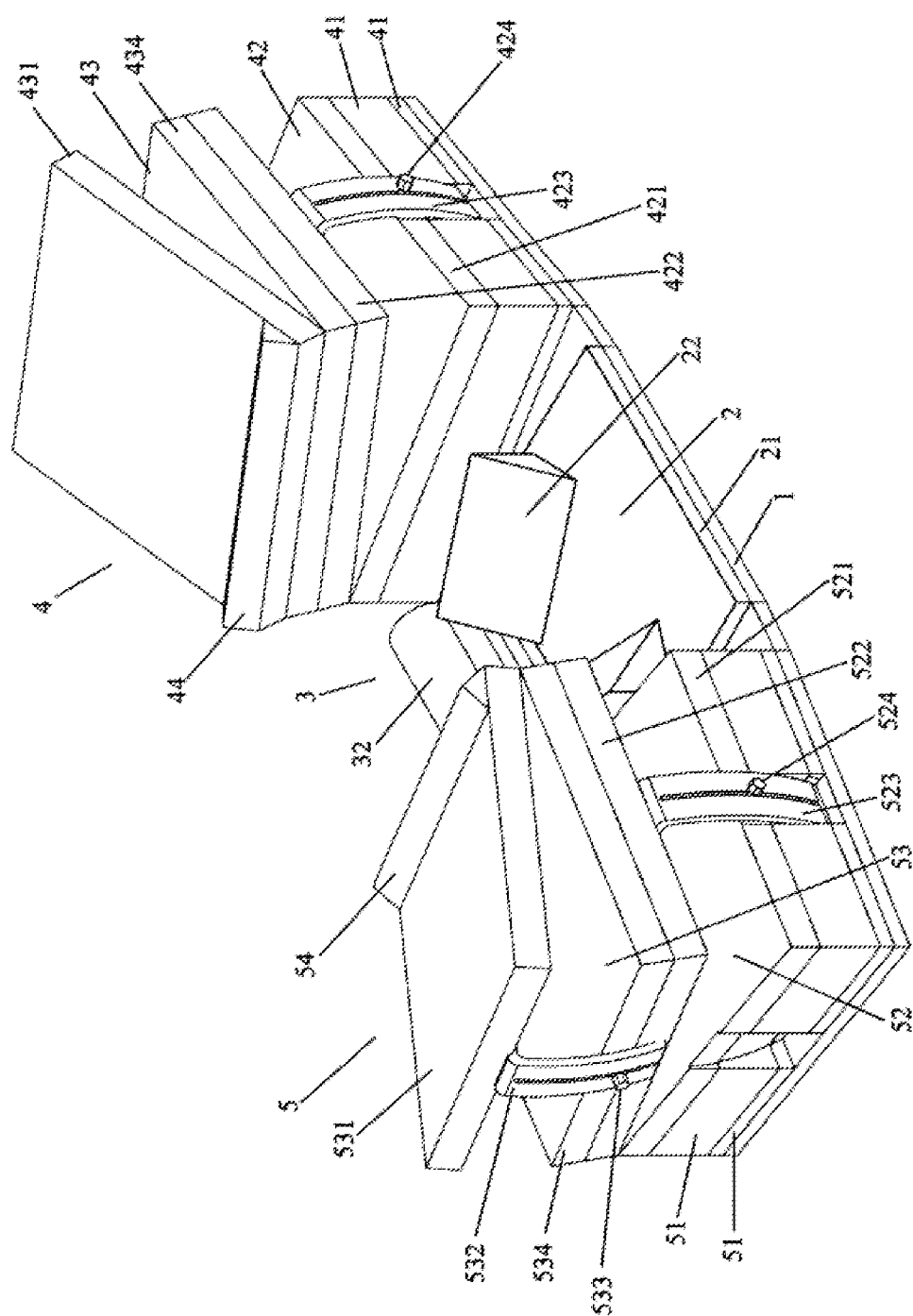
FIG. 7 is the schematic of the supporting bar set of the bi-use pillow in this invention viewed from the left back direction.

FIG. 6 and FIG. 7 show the working mechanism of the respective supporting bar set of the mechanism enabling adjustment to fit the vertebra curvature (52,42) and the mechanism enabling adjustment to inhibit too great an angle of lateral tilt (53,43) of the lateral recumbency pillows.

The supporting bar (523,423) and the fastening screw (524, 424) are mounted on the mechanism enabling adjustment to fit the vertebra curvature (52, 42). The arch section of the supporting bar (523,423) is fastened on the bottom panel of the working panel (522,422). A slot is cut along the centerline of the arch section for the fastening screw (524,424) to screw through. The nailhead on the fastening screw (524,424) can be resembled and dissembled by hand and the nailhead is fastened on the rear of the base board (521,421).

The supporting bar (532,432) and the fastening screw (533, 433) are mounted on the mechanism enabling adjustment to inhibit too great an angle of lateral tilt. The arch section of the supporting bar (532,432) is fastened on the bottom of the working panel (531,431). A slot is cut along the centerline of the arch section of the supporting bar for the fastening screw (533,433) to screw through. The nailhead of the fastening screw (533,433) can be resembled and dissembled by hand and the nailhead is fastened on the outer side of the base board (534,434).

In this preferred embodiment, to screw the fastening screw through the slot along the centerline of the arch section of the supporting bar (523,423) by hand to make a slope high at the back and low at the front on the working panel (522,422) of the mechanism enabling adjustment to fit vertebra curvature (52,42) around the hinge. The inclination of the working panel (531,431) of the mechanism enabling adjustment to inhibit too great an angle of lateral tilt (53,43) can be adjusted by screwing the fastening screw (533,433) through different slot holes on the supporting bar (532,432) of the mechanism enabling adjustment to inhibit too great an angle of lateral tilt (53,43). And the working panel (531,431) can be adjusted to a position high at the outer side and low at inner side and inclined downward towards the supine pillow (2) to achieve an inclination.

In this preferred embodiment, when it's necessary to separate the mechanism enabling adjustment to fit the vertebra curvature (52, 42) out and move it to the position between area B, A of the base board 1 and the bottom of the height adjustment members (51, 41) or between any of the two height adjustment members (51, 41) of the lateral recumbency pillow, the supporting bar (523,524) may be too long and collided with the base board or the bed. This problem can be solved by rotating the mechanism enabling adjustment to fit vertebra curvature (52, 42) around the inner edge of the base board (521,421) and making the end of the supporting bar pointing upward.

1.5 Optional Set 1.5.1 Slide Stop for Preventing the Head Slide on the Lateral Recumbency Pillow.

This invention also includes slide stop (54,44) which is set close to the inner edge of the bi-use pillow at the surface of the working panel (531,431)of the mechanism enabling adjustment to inhibit too great an angle of lateral tilt (53,43).

The slide stop (54,44) in this invention can be a three prism or a quarter of a cylinder which can avoid the feeling of sliding along the slope on the working panel (531,431)of the mechanism enabling adjustment to inhibit too great an angle of lateral tilt (53,43) while the sleeper rest the head on the lateral recumbency pillow.

1.5.2 Rounded Rectangle Holes for Ears

In this invention of bi-use pillow, there is a rounded rectangle of 8 cm*6 cm in longitudinal direction in the middle of the upper layer of the external cushion of the right and left lateral recumbency pillow (5, 4) respectively for ears to put in. When rest the head on the lateral recumbency pillow the sleeper can put the ear in the rectangle to release the pressure of the ear and make the tissue around ear bear the weight of the head evenly. This can protect the ears and the tissue around them.

1.5.3 Pressure Sensor, Electronic Timer and Sound LCD

In order to guarantee the sleeper spend roughly equal time on the left and right lateral recumbency pillow (5, 4), a pressure sensor can be attached to sense the lateral condition of the sleeper. The pressure sensor can be set between any of the two planks of the left and right lateral recumbency pillow (5, 4) or in the mezzanine of a separate thin sheet. And also a timer is attached to the bi-use pillow to accumulate the time the sleeper spend on the left and right lateral recumbency pillows (5,4) respectively. The timer can be put inside any of the height adjustment members or outside of the bi-use pillows. And according to the difference in time a sound LCD instructor can be mounted on the bi-use pillow and give use of guidance according to the principle of that the time the sleeper spends on left and right recumbency pillows (5, 4) should be roughly the same. The sound LCD instructor includes speaker and LCD. The speaker can remind the sleeper to sleep on both sides through sound and is mounted in the rounded rectangle on the external cushion for putting ears. Or the LCD can be used for the same purpose. The pressure sensor, electronic sensor and sound and light electronic instructor can be control by a microcomputer.

With the material and technology allowing, thinner planks should be adopted when making the base board (1) and the base boards and working panels of the mechanism enabling adjustment to fit vertebra curvature (52,42) and mechanism enabling adjustment to inhibit too great an angle of lateral tilt (53,43) in order to eliminate the total height of the components of the left and right lateral recumbency pillow (5,4) other than the height adjustment members (51,41) and the height of the lateral recumbency pillow (5,4) can be adjusted by add more height adjust members (51,41). The adjustable height range of the lateral recumbency pillows (5,4) can be enlarged in this way. When the bi-use pillow is for children planks of smaller size which are thinner than 0.3 cm should be adopted when making the base board (1), base board (521, 421) and working panel (522,422) of the mechanism enabling adjustment to fit vertebra curvature (52,42), and base board (534,434) and working panel (531,431)*of* the mechanism enabling adjustment to inhibit too great an angle of lateral tilt (53,43). Base board (1) and angle adjustment set (51, 41) should be made of material with high strength and is not easy to deform or break. Lighter material such as high density sponge and EVA should be adopted when making all kinds of the height adjustment components.

Preferred embodiment 2: the use and adjustment of the universally adjustable pillow for use in healthcare and therapy.

This invention of bi-use pillow should be adjusted according to the requirements of different user. There are adjustments for lateral recumbency, for supine recumbency and for flexible application.

2.1 Adjustment for Lateral Recumbency Position.

The adjustment for lateral recumbency includes height adjustment, angle adjustment and the setting of electronic reminder wear.

2.1.1 Height and Angle Adjustment

Remove the pillow and let the sleeper sleep on his back, or let the sleeper sit or stand up and relax the shoulders while keeping the head straight. Then measure the vertical distance between the lateral shoulder and ipsilateral zygomatic on the transverse section of the body and record the measured data. Adjust the total height of the lateral recumbency pillows (4, 5) and the base board (1) to the measured data by adjusting the height adjustment members of the lateral recumbency pillows. Adjust the angle of the lateral recumbency pillows (4, 5) that complies to the vertebra curvature to 15 degree. Adjust the angle inhibits lateral tilt to 5 degree. Let the sleeper rest at the lateral recumbency pillow (4, 5) and to see whether the cervicothoracic junction on the spine is straight (it is acceptable for the overall spine to curve slightly), whether there is distortion on the spine or whether the shoulder blade is displaced Tuning the height and the angle that complies to the vertebra curvature of the lateral recumbency pillow (4, 5) according to the practical situation to make sure that the cervicothoracic junction on the spine is straight and there is no distortion on the spine. And to make sure that there is no pressure on the shoulder. The adjustment of the angle inhibits lateral tilt is totally base on the sleeper's feelings. If the angle is too small the purpose of inhibiting a lateral tilt will not be achieved and if the angle is too large the sleeper will feel uncomfortable. A balance point should be sought between the just mentioned situations. The angle should be adjusted to a degree which can make the sleeper feel comfortable without lateral tilt. The slide stop (44, 54) can be moved a bit towards the inner or outer edge. The slide stop (44, 54) can be removed if there is no tendency of sliding on the lateral recumbency pillow. The adjusted height and angles of the right and left lateral recumbency pillows can be different.

2.1.2 Adjustment of the Electronic Reminder

When the sleeper sleep on the lateral recumbency pillows the pressure sensor will be triggered and send a signal to the microcomputer. The microcomputer will collect this signal and command the electronic timer to calculate the duration of signal and automatically compare the data of both sides. A suggestion will be displayed on the LCD of the microcomputer for the sleeper's reference. And the speaker in the rounded rectangle for ears will make a sound to remind the sleeper. There are 5 types of program to fulfill the needs of different sleepers.

1) Common sleeper: It refers to sleepers who spend roughly the same time on the left and right lateral recumbency pillows. If the sleeper rest on one of the lateral recumbency pillow 16 hours more than the time he spend on the other one, the LCD will remind the sleeper that it is allowed to rest on both of the lateral recumbency pillow and it is suggested to rest on the one less used. And the speaker will make a sound when the sleeper first uses the lateral recumbency pillow every night or during a nap. If the sleeper ignore the message and rest on one of the lateral recumbency pillow 24 hours more than the time he spend on the other one, the LCD will display "forbidden" on the much used side and "recommended" on the less used side. Once the sleeper rests on the much used lateral recumbency pillow the speaker in it will make a repeated sound with an increasing volume to force the sleeper to use the other side.

2. Sleepers who more used to sleep on the right side: In this case the pillow will urge the sleeper to sleep on the left side more often. The program require the total time the sleeper rest on the left lateral recumbency pillow is 1-2 times more than he spend on the other side (not too much nor too little). If this requirement is not fulfilled the LCD will still display "allow" on the much used side while display "recommended" on the less used side. And the speaker will make a sound when the sleeper first uses the lateral recumbency pillow every night or during a nap. If the sleeper ignore the message and make the ratio of the two side further deviate the requirement, the LCD will display "forbidden" on the much used side and "recommended" on the less used side. Once the sleeper rests on the much used lateral recumbency pillow the speaker in it will make a repeated sound with an increasing volume to force the sleeper to use the other side or sleep on his back.

3) Sleepers who more used to sleep on the left side: In this case the pillow will urge the sleeper to sleep on the right side more often. The program require the total time the sleeper rest on the right lateral recumbency pillow is 1-2 times more than he spend on the other side (not too much or too little). If this requirement is not fulfilled the LCD will still display "allow" on the much used side while display "recommended" on the less used side. And the speaker will make a sound when the sleeper first uses the lateral recumbency pillow every night or during a nap. If the sleeper ignore the message and make the ratio of the two side further deviate the requirement, the LCD will display "forbidden" on the much used side and "recommended" on the less used side. Once the sleeper rests on the much used lateral recumbency pillow the speaker in it will make a repeated sound with an increasing volume to force the sleeper to use the other side or sleep on his back.

4. Sleepers who always sleep on the right side: In this case the electronic reminder wear will suggest the sleeper not to sleep on the right side and sleep on the left side or on the back instead. The LCD display "forbidden" on the right side and "recommended" on the left side. Once the sleeper rests on the right lateral recumbency pillow the speaker in it will make a repeated sound with an increasing volume to force the sleeper to use the other side or sleep on his back. One year later turn to program 2.

5 Sleepers who always sleep on the left side: In this case the electronic reminder wear will suggest the sleeper not to sleep on the left side and sleep on the right side or on the back instead. The LCD display "forbidden" on the left side and "recommended" on the right side. Once the sleeper rests on the left lateral recumbency pillow the speaker in it will make a repeated sound with an increasing volume to force the sleeper to use the other side or sleep on his back. One year later turn to program 3.

The parameters of the above mentioned program can be set according to different situations. The speaker of the electronic reminder wear can be turn off and the volume is adjustable. When the sleeper lost the ability to perform an activity or is unconscious the speaker should be turn off. The medics will decide the position of the patient according to care principals and the suggestion displayed on the LCD 2.2 Adjustment for Supine Recumbency There are supine recumbency adjustment for common sleepers and treatments. In both cases height adjustment for supine recumbency pillow (2) and neck pillow (3), position adjustment for supine neck pillow (3) and fixation cushion (22) are included. Thereof the neck pillow (3) is mainly used to adjust the cervical lordosis and can be moved back and forth according to the sleeper's body form. The neck pillow (3) can be placed at the back of middle cervical or posterior cervical that need particular treatment. The height adjustment of supine recumbency pillow (2) and neck pillow (3) can take the pillow for daily use for reference. In the case of treatment a use plan for gradual progress should be made according to the patient's condition. There are fixation cushions (22) placed on both sides of the head to prevent the head turning aside and improve the stability. The fixation cushions can be moved fore-aft and the angle between the two sides can be adjusted freely to make the sleeper feel comfortable. Some sleeper's head is not symmetry so it's not necessary for the fixation cushions to be placed symmetry.

2.2.1 Common Sleeper

For common sleeper, the height adjustment members (21) of the supine recumbency pillow (2) can be removed and the sleeper can rest on the external cushion glued on the base board (1). Most people keeps his head down in day time at work that will make the cervical Lordosis prone to disappear or even curve to the opposite direction. If the neck suspends on the pillow while the sleeper is in supine position the weight of the neck will drag the cervical towards the bed. This can make the cervical lordosis disappear. Neck pillow (3) can be adjusted to proper height to avoid this situation and make the back of head rest comfortably on the pillow.

Some sleeper especially elder people are used to high pillow in supine position. If the pillow is removed abruptly the sleeper may feel uncomfortable. In this case the height of the supine recumbency pillow should be reduced gradually.

When use the neck pillow (3) inadaptability syndrome may occur such as numbness, nausea or dizziness ect, because the neck pillow is too high. In this case stop using the pillow immediately. If the condition is not improved by lowering the pillow please consult the medics staff.

2.2.2 for Treatment

The pillow can be used in treatment for all kinds of cervical spondylosis, cervical disc herniation, stiff neck, repeated shoulder pain, bedridden person, cervicogenic headache, cervical traction in supine position, snoring, sleep apnea and orthotics. Patients of cervical spine fracture, cervical cancer, cervical tuberculosis or other severe neck disorders especially bone disease, severe spinal diseases or severe vertebral artery and carotid disease is prohibited to use this pillow or use this pillow with caution. Specific indications, contraindications or treatment progress should be decided and judged by medics according to patient's condition.

The principles for pillow adjustment are making gradual adjustment according to the condition and avoiding excessive adjustment for every adjustment (especially in supine position)

2.3 Adjustment for Flexible Application

This invention can be adjusted with high degree of flexibility. All the components of the pillow can be removed and assembled for more convenient application.

Take the following situation for example:

2.3.1 Remove Lateral Recumbency Pillow on One Side

One of the lateral recumbency pillows (5, 4) can be removed to observe the usage of neck pillow (3) and supine recumbency pillow (2) more clearly when it's necessary.

2.3.2 the Display Order and Position of Different Layers of the Lateral Recumbency Pillow can be Changed Except the base board and working panel of the angle adjustment mechanism of the lateral recumbency pillow, any of the two adjacent layers of the bi-use pillow are connected by the hook and loop fasteners. Both the barb and brush side of the hook and loop fastener are square. The size of one side is small which is 1 cm$^2$. The size of the other side is large which is 9 cm$^2$. The barb and brush side of the hook and loop fastener can also be a rectangle size of 5 cm*1 cm and are stuck together vertically. This can guarantee that the contact area of the hook and loop fastener remains 1 cm$^2$ and the adhesion force of the hook and loop fastener will not effected by minor dislocation of the two layers The shoulder may conflict the bottom part of the lateral recumbency pillow when the sleeper is sleeping on back. In this case the head can not be fully rest on the surface of the lateral recumbency pillows. This problem can be solved by enlarge the distance between the shoulder on the bed side and the lateral recumbency pillows of the same side. Take right lateral recumbency pillows (4) on area (A) of the base board (1) for example to explain the specific methods. The mechanism enabling adjustment to fit vertebra curvature (42) of the lateral recumbency pillow (4) can be separated out and placed between area A of the base board (1) and the bottom of the height adjustment members (41) in order to make the whole lateral recumbency pillow incline forward. Or place the mechanism (42) between any two of the height adjustment members (41) and make the components above it incline forward. And/or any one or more of the height adjustment members (41) of the lateral recumbency pillows (4), angle adjustment mechanism (42,43) and external cushion can be staggered with reference to the layer below it. The space between the shoulder near the bed and the lateral recumbency pillow on the same side can be enlarged effectively so that the surface of the lateral recumbency pillow (4) can stuck in. In this way the lateral recumbency pillow (4) can fully bear the weight of the head.

If the sleeper's head is rather large and the supine recumbency pillow is not wide enough the lateral recumbency pillow can be dissembled from the base board and move outward a bit before gluing on the base board again. The supine recumbency pillow will be wider by doing this.

In one of the preferred embodiment of this invention the right rolling angle α and left rolling angle β which complying the vertebra are pre-set at 10 degree. In practical use if the angle is too small or too big the lateral recumbency pillows can be dissembled from the base board and re-assembled on the base board after rotating a bit.

2.3.3 the Base Board can be Removed

Remove the base board (1) so that the lateral recumbency pillow (4, 5), supine recumbency pillow (2) and neck pillow (3) can be moved freely and used separately or make any combination For the bedridden sleeper who lost the ability to perform a activity and is unconscious the base board (1) can be removed in order to use the lateral recumbency pillow (4, 5), supine recumbency pillow (2) and neck pillow (3) separately. In this way when the patient uses one of the components the other components of the pillow will not impede care treatment.

If the bed is extremely narrow, one side of lateral recumbency pillow can be removed. Adjust the angle that inhibit lateral tilt of the other lateral recumbency pillow to 0 and remove the slide stop. In this way the lateral recumbency pillow can be used for both left and right recumbency.

2.3.4. The Pillow can be Used by Couples.

The couple can sleep face to face. Then use the methods mentioned in 2.3.2 to enlarge the space between the wife's shoulder on bed and the lateral recumbency pillow of the same side so that there is enough space for the husband's arm to pass under and hold the wife This invention is aimed at maintaining a normal biological makeup and functional status of human body while sleeping on one's side or on back. It can be used for any person in theory. (Children under 8 or people who are pro-active are banned from using this pillow because they can not act according to the instruction and may cause injure. Supervision is needed when unconscious patient uses this invention)

I claim:

1. A universally adjustable pillow for use in healthcare and therapy comprising a first base board, and a right lateral recumbency pillow, a supine recumbency pillow, a left lateral recumbency pillow and a neck pillow that are arranged on the first base board, wherein the right lateral recumbency pillow is on a right side of the supine recumbency pillow, the left lateral recumbency pillow is on a left side of the supine recumbency pillow and the neck pillow is on a front of the supine recumbency pillow; wherein both the left and the right lateral recumbency pillows comprise a plurality of connected height adjustment members, a mechanism enabling adjustment to fit vertebral curvature, and a mechanism enabling adjustment to inhibit too great an angle of lateral tilt, wherein longitudinal axes of the left and the right lateral recumbency pillows are set at an angle to a longitudinal axis of the supine recumbency pillow;

wherein the mechanism enabling adjustment to fit vertebra curvature and the mechanism enabling adjustment to inhibit too great an angle of lateral tilt of the left and the right lateral recumbency pillows are carried out though angle adjustment bar sets or supporting bar sets, wherein the angle adjustment bar set of the mechanism enabling adjustment to fit vertebra curvature of the right and the left lateral recumbency pillows comprises a second base board, a first working panel, a first hinge and a first angle adjustment bar, wherein an inner edge of the first working panel and an inner edge of the second base board are connected by the first hinge, and between outer sides of the first working panel and the second base board set the first angle adjustment bar which is parallel with a back edge of the second base board; and the angle adjustment bar set of the mechanism enabling adjustment to inhibit too great an angle of lateral tilt comprises a third base board, a second working panel, a second hinge and a second angle adjustment bar, wherein an inner edge of the second working panel and an inner edge of the third base board are connected by the second hinge, and between outer sides of the second working panel and the third base board set the second angle adjustment bar which is parallel with an outer edge of the third base board; or the supporting bar set of the mechanism enabling adjustment to fit the vertebra curvature of the right and the left lateral recumbency pillows comprises a fourth base board, a third working panel, two third hinges, a first supporting bar and a first fastening screw, wherein the two third hinges are mounted on front edges of the fourth base board and the third working panel, and an arch section of the first supporting bar is fixed on a bottom panel at a back of the third working panel, and a first slot is cut along a centerline of a vertical arch section of the first supporting bar for the first fastening screw to screw through, and the first fastening screw has a nailhead which can be removed and mounted by hand and the nailhead is fastened at a rear of the fourth base board; and the supporting bar set of the mechanism enabling adjustment to inhibit too great an angle of lateral tilt of the right and the left lateral recumbency pillows comprises a fifth base board, a fourth working panel, two fourth hinges, a second supporting bar and a second fastening screw, wherein an inner edge of the fifth base board and an inner edge of the fourth working panel are connected by the two fourth hinges, and an arch section of the second supporting bar is fixed on a bottom of an outer side of the fourth working panel, and a second slot is cut along a centerline of a vertical arch section of the second supporting bar for the second fastening screw to screw through, and the second fastening screw has a nailhead which can be removed and mounted by hand which is fastened on an outer side of the fifth base board.

2. The pillow, as recited in claim 1, wherein the mechanism enabling adjustment to fit the vertebra curvature is glued between the lateral recumbency pillows' height adjustment members and the mechanism enabling adjustment to inhibit too great an angle of lateral tilt, or between the first base board and the lateral recumbency pillows' height adjustment members, or between any two of the lateral recumbency pillows' height adjustment members.

3. The pillow as recited in claim 1, wherein a first guide is set vertically under the first angle adjustment bar of the mechanism enabling adjustment to fit vertebra curvature and a second guide is set vertically under the second angle adjustment bar of the mechanism enabling adjustment to inhibit too great an angle of lateral tilt respectively; correspondingly a first notch is cut on the second base board of the mechanism enabling adjustment to fit vertebra curvature and a second notch is cut on the third base board of the mechanism enabling adjustment to inhibit too great an angle of lateral tile, wherein the first guide and the second guide are respectively embedded in the first notch and the second notch to slide freely, and tops of the angle adjustment bars of the mechanism enabling adjustment to fit the vertebra curvature and the mechanism enabling adjustment to inhibit too great an angle of lateral tilt are glued through adhesive wears to bottoms of the working panels of the two mechanisms.

4. The pillow as recited in claim 1, wherein an adjustable range of the mechanism enabling adjustment to fit the vertebra curvature is 5-25 degree, and an adjustable range of the mechanism enabling adjustment to inhibit too great an angle of lateral tilt is 0-15 degree.

5. The pillow as recited in claim 1, wherein there is a rounded rectangle of 8 cm*6 cm on an external cushion for putting ears of each of the right and the left lateral recumbency pillows respectively.

6. The pillow, as recited in claim 1, wherein a pressure sensor is attached to the right and the left lateral recumbency pillows to sense a lateral condition of a sleeper, and also an electronic timer is attached to the pillow to accumulate a time the sleeper rests on the right lateral recumbency pillow and the left lateral recumbency pillow respectively, and according to a difference in time a sound LCD instructor provides guidance for the sleeper, wherein the pressure sensor, the electronic timer and the sound LCD instructor are controlled by a microcomputer;
  wherein the sound LCD instructor comprises a speaker and an LCD, and the speaker is mounted in a rounded rectangle on external cushions for putting ears of the right lateral recumbency pillow and the left lateral recumbency pillow.

7. The pillow, as recited in claim 1, wherein the angle is ≤20 degree.

8. The pillow, as recited in claim 1, further comprising a right side slide stop and a left side slide stop to prevent a sleeper from dropping from the pillow, wherein the two slide stops are glued on inner sides on surfaces of the right and the left lateral recumbency pillows respectively.

9. The pillow, as recited in claim 1, wherein the supine pillow comprises 1-3 pieces of height adjustment members each with a thickness of 1 cm-4 cm and an external cushion, and on upper and bottom sides of every height adjustment member there is an adhesive wear for aligning and mounting together; and
  the pillow further comprises two fixation cushions having adhesive on bottoms to which is glued the supine recumbency pillow.

10. The pillow, as recited in claim 1, wherein the neck recumbency pillow comprises 1-3 pieces of height adjustment members each with a thickness of 1 cm-4 cm and a neck column, wherein an upper part of the neck column is a half cylinder and a bottom part of the neck column is a pillar, and the height adjustment members are stacked together through hook and loop fasteners on a top and bottom of each member, and the top of the height adjustment member is glued on a bottom of the neck column through the hook and loop fastener and the bottom of height adjustment member is glued to the first base board through an adhesive wear, and a cross-section of the upper part of the neck column which is the half cylinder has a radius of 2 cm and a cross section of the bottom part which is the pillar has a rectangle size of 4 cm*2 cm, and a size of the height adjustment member is 15*6 cm, and a size of the height adjustment member is 15 cm*6 cm.

11. The pillow, as recited in claim 1, wherein each of the right and the left lateral recumbency pillows comprises 1-4 pieces of the height adjustment members having a height of 1 cm-5 cm which are stacked together by hook and loop fasteners on each member's top and bottom and an undermost height adjustment member is glued on the first base board by the hook and loop fastener.

12. A universally adjustable pillow for use in healthcare and therapy comprising a first base board, and a right lateral recumbency pillow, a supine recumbency pillow, a left lateral recumbency pillow and a neck pillow that are arranged on the first base board, wherein the right lateral recumbency pillow is on a right side of the supine recumbency pillow, the left lateral recumbency pillow is on a left side of the supine recumbency pillow and the neck pillow is on a front of the supine recumbency pillow; wherein both the left and the right lateral recumbency pillows comprise a plurality of connected height adjustment members, a mechanism enabling adjustment to fit vertebral curvature, and a mechanism enabling adjustment to inhibit too great an angle of lateral tilt, wherein longitudinal axes of the left and the right lateral recumbency pillows are set at an angle to a longitudinal axis of the supine recumbency pillow;
  wherein the mechanism enabling adjustment to fit vertebra curvature and the mechanism enabling adjustment to inhibit too great an angle of lateral tilt of the left and the right lateral recumbency pillows are carried out though angle adjustment bar sets or supporting bar sets, wherein the angle adjustment bar set of the mechanism enabling adjustment to fit vertebra curvature of the right and the left lateral recumbency pillows comprises a second base board, a first working panel, two first hinges and a first angle adjustment bar, the second base board is glued to the height adjustment member by an adhesive wear, and a front edge of the second base board and a front edge of the first working panel are connected by the two first hinges, and between back sides of the first working panel and the second base board set the first angle adjustment bar which is parallel with a back edge of the second base board; and the angle adjustment bar set of the mechanism enabling adjustment to inhibit too great an angle of lateral tilt comprises a second working panel, a second hinge and a second angle adjustment bar, wherein an inner edge of the second working panel and an inner edge of the first working panel of the mechanism enabling adjustment to fit vertebra curvature are connected by the second hinge, and between outer sides of the first working panel and the second working panel set the second angle adjustment bar which is parallel with an outer edge of the first working panel of the mechanism enabling adjustment to fit vertebra curvature; or
  the supporting bar set of the mechanism enabling adjustment to fit the vertebra curvature of the right and the left lateral recumbency pillows comprises a third base board, a third working panel, two third hinges, a first supporting bar and a first fastening screw, wherein the two third hinges are mounted on front edges of the third base board and the third working panel, and an arch section of the first supporting bar is fixed on a bottom panel at a back of the third working panel, and a first slot is cut along a centerline of a vertical arch section of the first supporting bar for the first fastening screw to screw through, and the first fastening screw has a nailhead which can be removed and mounted by hand and the nailhead is fastened at a rear of the third base board; and the supporting bar set of the mechanism enabling adjustment to inhibit too great an angle of lateral tilt of the right and the left lateral recumbency pillows comprises a fourth working panel, a fourth hinge, a second supporting bar and a second fastening screw, wherein an inner edge of the fourth working panel and an inner edge of the third working panel of the mechanism enabling adjustment to fit vertebra curvature are connected by the fourth hinge, and an arch section of the second supporting bar is fixed on a bottom of an outer side of the fourth working panel, and a second slot is cut along a centerline of a vertical arch section of the second supporting bar for the second fastening screw to screw through, and the second fastening screw has a nailhead which can be removed and mounted by hand which is fastened on an outer side of the third working panel of the mechanism enabling adjustment to fit the vertebra curvature.

13. The pillow, as recited in claim 12, wherein an adjustable range of the mechanism enabling adjustment to fit the vertebra curvature is 5-25 degree, and an adjustable range of the mechanism enabling adjustment to inhibit too great an angle of lateral tilt is 0-15 degree.

14. The pillow, as recited in claim 12, wherein there is a rounded rectangle of 8 cm*6 cm on an external cushion for putting ears of each of the right and the left lateral recumbency pillows respectively.

15. The pillow, as recited in claim 12, wherein a pressure sensor is attached to the right and the left lateral recumbency pillows to sense a lateral condition of a sleeper, and also an electronic timer is attached to the pillow to accumulate a time the sleeper rests on the right lateral recumbency pillow and the left lateral recumbency pillow respectively, and according to a difference in time a sound LCD instructor provides guidance for the sleeper, wherein the pressure sensor, the electronic timer and the sound LCD instructor are controlled by a microcomputer;

wherein the sound LCD instructor comprises a speaker and an LCD, and the speaker is mounted in a rounded rectangle on external cushions for putting ears of the right lateral recumbency pillow and the left lateral recumbency pillow.

16. The pillow, as recited in claim 12, wherein the angle is ≤20 degree.

17. The pillow, as recited in claim 12, further comprising a right side slide stop and a left side slide stop to prevent a sleeper from dropping from the pillow, wherein the two slide stops are glued on inner sides on surfaces of the right and the left lateral recumbency pillows respectively.

18. The pillow, as recited in claim 12, wherein the supine pillow comprises 1-3 pieces of height adjustment members each with a thickness of 1 cm-4 cm and an external cushion, and on upper and bottom sides of every height adjustment member there is an adhesive wear for aligning and mounting together; and the pillow further comprises two fixation cushions having adhesive on bottoms to which is glued the supine recumbency pillow.

19. The pillow, as recited in claim 12, wherein the neck recumbency pillow comprises 1-3 pieces of height adjustment members each with a thickness of 1 cm-4 cm and a neck column, wherein an upper part of the neck column is a half cylinder and a bottom part of the neck column is a pillar, and the height adjustment members are stacked together through hook and loop fasteners on a top and bottom of each member, and the top of the height adjustment member is glued on a bottom of the neck column through the hook and loop fastener and the bottom of height adjustment member is glued to the first base board through an adhesive wear, and a cross-section of the upper part of the neck column which is the half cylinder has a radius of 2 cm and a cross section of the bottom part which is the pillar has a rectangle size of 4 cm*2 cm, and a size of the height adjustment member is 15*6 cm, and a size of the height adjustment member is 15 cm*6 cm.

20. The pillow, as recited in claim 12, wherein each of the right and the left lateral recumbency pillows comprises 1-4 pieces of the height adjustment members having a height of 1 cm-5 cm which are stacked together by hook and loop fasteners on each member's top and bottom and an undermost height adjustment member is glued on the first base board by the hook and loop fastener.

* * * * *